United States Patent [19]

Jones et al.

[11] Patent Number: 5,619,889

[45] Date of Patent: Apr. 15, 1997

[54] METHOD OF MAKING MICROSTRUCTURAL SURGICAL INSTRUMENTS

[75] Inventors: Gary W. Jones, Poughkeepsie; Steven M. Zimmerman, Pleasant Valley, both of N.Y.

[73] Assignee: FED Corporation, Hopewell Junction, N.Y.

[21] Appl. No.: 321,089

[22] Filed: Oct. 11, 1994

[51] Int. Cl.$^6$ ............................................. B24B 1/04
[52] U.S. Cl. ................................. 76/104.1; 451/165
[58] Field of Search ............................. 30/350, 346.54; 76/101.1, 104.1; 451/36, 165

[56] References Cited

U.S. PATENT DOCUMENTS

| | | | |
|---|---|---|---|
| 4,934,103 | 6/1990 | Campergue et al. | 451/165 |
| 5,193,311 | 3/1993 | Dawson | 451/165 |
| 5,317,938 | 6/1994 | Juan, Jr. | 76/104.1 |

Primary Examiner—Douglas D. Watts
Attorney, Agent, or Firm—Intellectual Property/Technology Law; John P. McMahon

[57] ABSTRACT

A method of making a microstructural shaped article from a high hardness substrate workpiece, in which an energy-transmissive shaping member is secured in energy-transmissive relationship to an energy source, and the substrate workpiece is positioned in alignment therewith. A fine grain slurry of solid particles is provided between the energy-transmissive shaping member and the substrate, and the substrate workpiece is milled by the energy-transmissive shaping member in compressive bearing relationship to the substrate through the fine grain slurry of solid particles, for sufficient time to form the desired shape in the substrate workpiece. A reusable, tribologically enhanced die is also described, for use in the method of the invention. The energy source may be an electroacoustic energy source or an electric power energy source. The non-etched microstructural articles of the invention include knives, saws, and other instruments useful for ocular and other surgical applications.

21 Claims, 10 Drawing Sheets

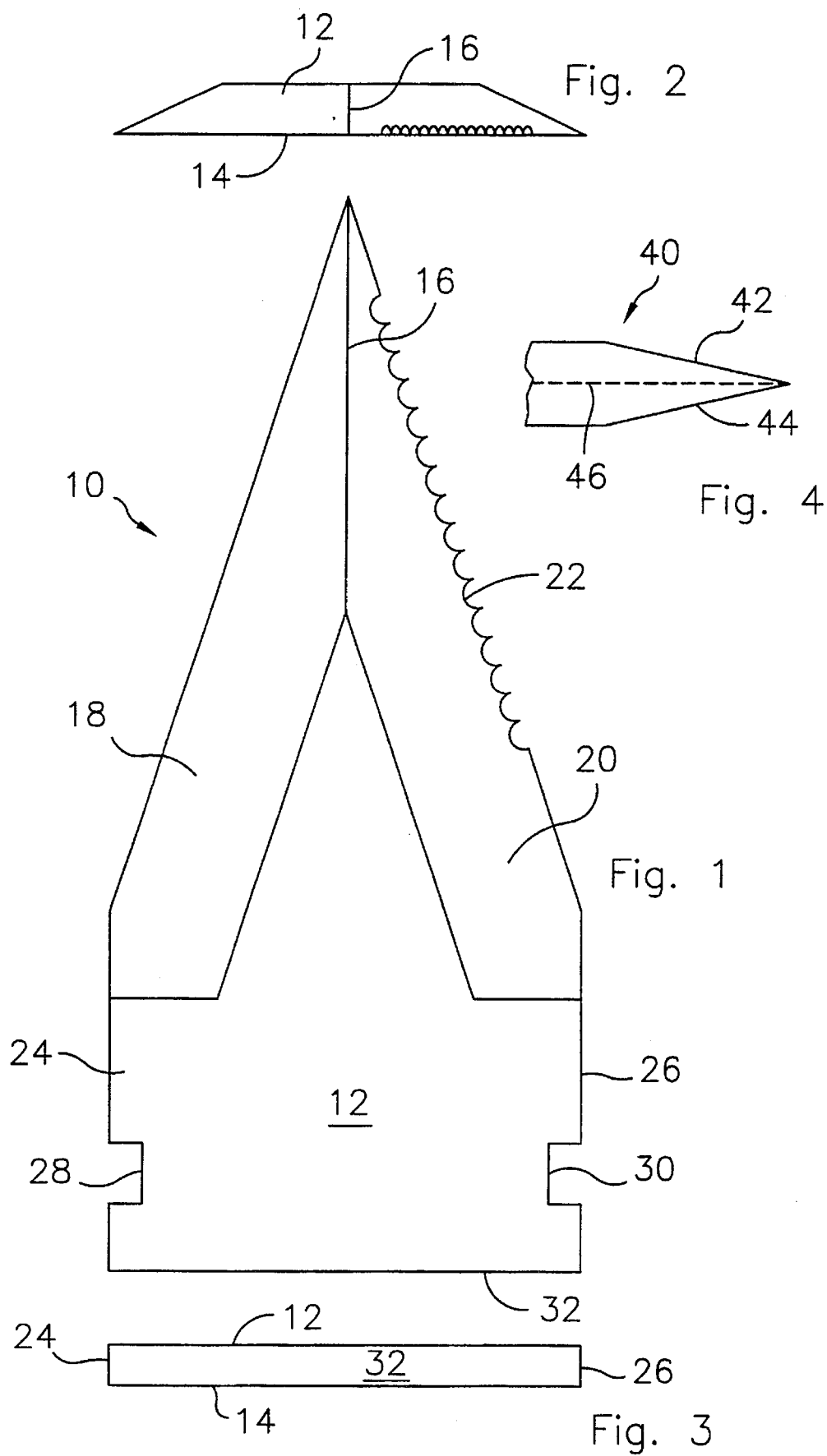

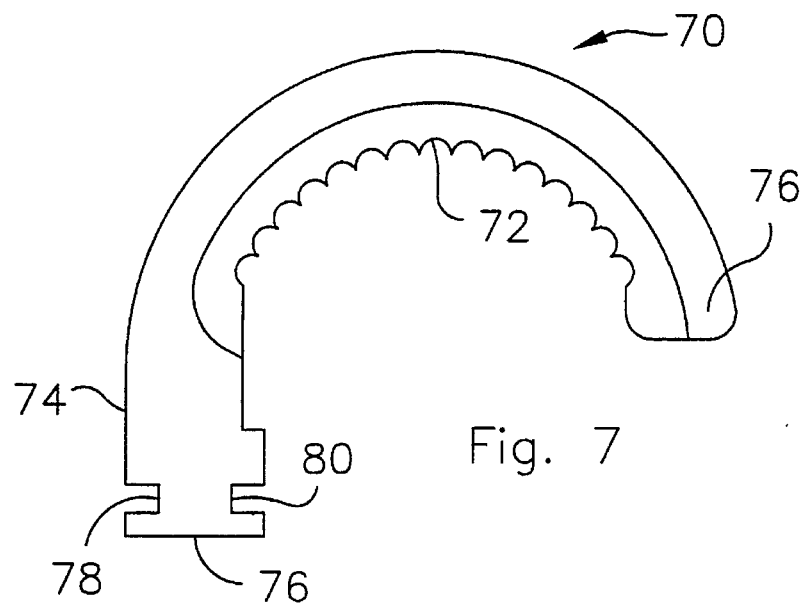
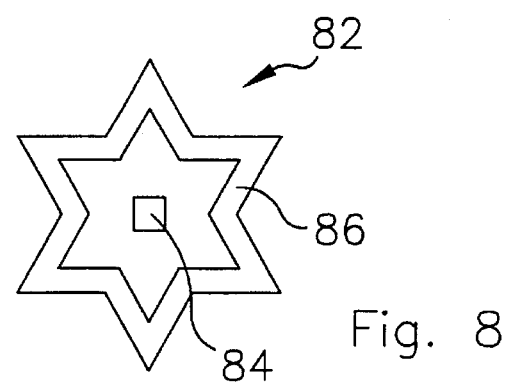
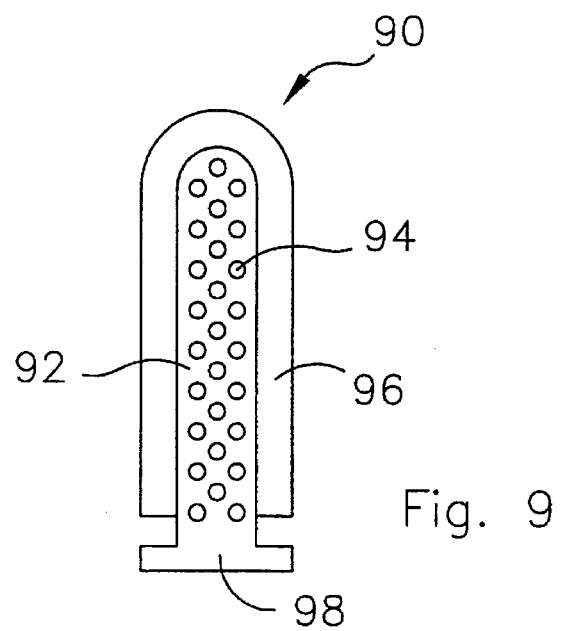

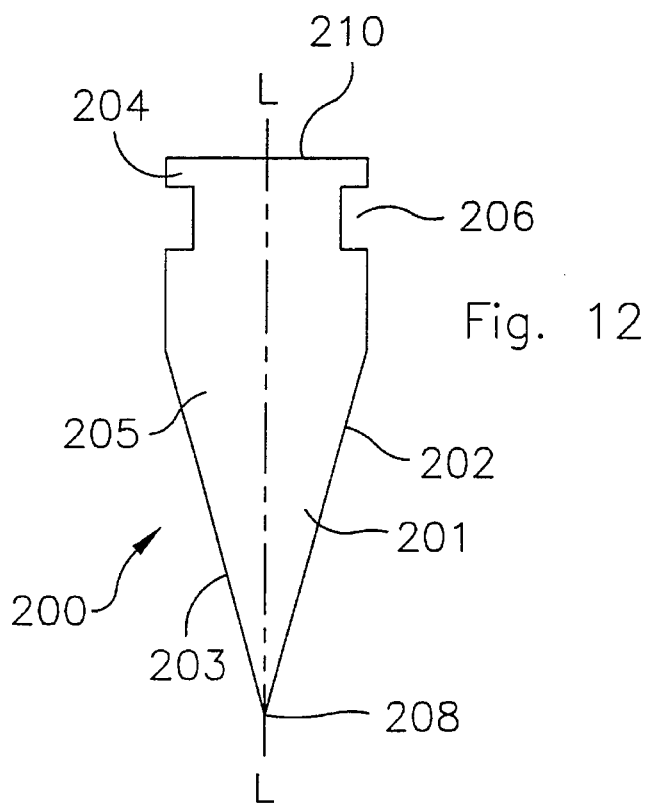
Fig. 12
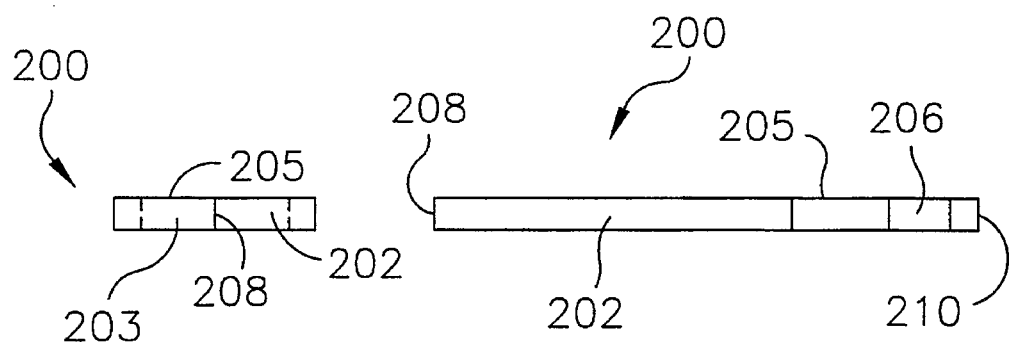
Fig. 13
Fig. 14

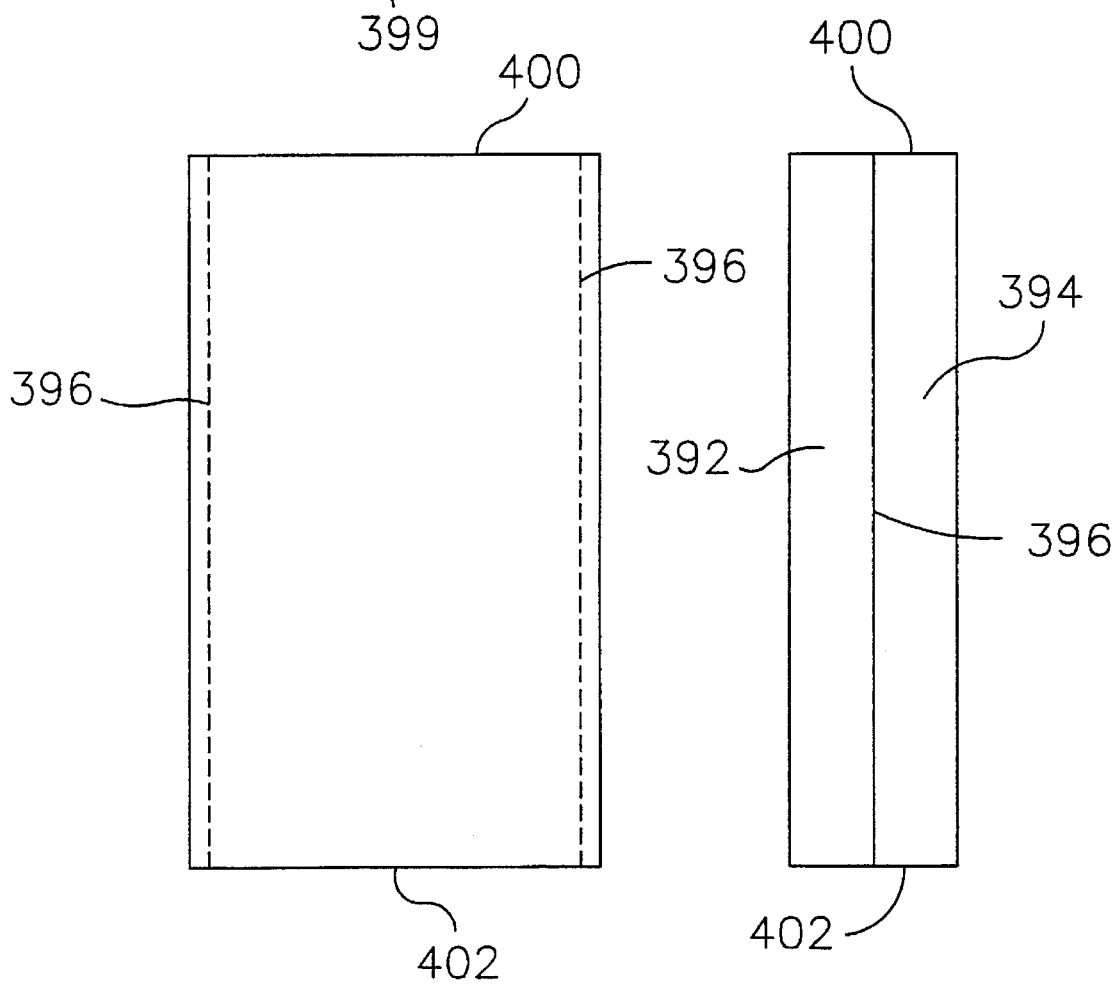

METHOD OF MAKING MICROSTRUCTURAL SURGICAL INSTRUMENTS

BACKGROUND OF THE INVENTION

1. Field of the Invention

The present invention relates to the design and manufacture of novel microstructural shaped articles, including micro instruments such as micro-knives, tweezers, saws, pins, clamps, and hooks from very hard and chemically inert materials at low cost suitable for microsurgery.

2. Description of the Related Art

In microsurgery such as ophthamological surgery, small, precision, mechanical structures with sharp cutting edges are needed. In addition, many shapes and cutting edge variations such as serrated knives and interocular saws are needed for specialized surgery in the region of the eye. Further, it is important that these instruments be made of a mechanically stable material that is both hard and durable.

Conventionally, these "edged" medical tools are either mass produced from metals such as tungsten or stainless steel, or hand ground from harder materials such as diamond, silicon and sapphire. The disposable metal knives are relatively blunt and wear quickly over time. The non-disposable diamond or sapphire knives, on the other hand, are expensive and brittle. Further, current techniques of fabricating these harder knives are unable to produce certain cutting edge variations such as serrations that are needed in this type of surgery.

In particular, the current manufacturing technology for hand-made instruments of the above-described type is not only expensive, but also is limited in its ability to produce important second order structures such as serrations and inside angles.

U.S. patent application Ser. No. 08/822,021 filed 16 January 1992 in the names of Gary W. Jones, et al., the disclosure of which is hereby incorporated herein, describes a lithographic pattern and etched structural method of making such types of microinstruments. This technique, while an advance in the art, nonetheless suffers from a number of associated deficiencies, as discussed below.

Sapphire, ruby and silicon carbide are very difficult and expensive to etch because of the etch chemistry required. Inert metal masks such as platinum or iridium are necessary. These masks must be sufficiently thick to withstand highly reactive etches with reagents such as molten potassium hydroxide. Further, such method requires very expensive etch vessels constructed of materials such as platinum that are slowly consumed during the process. Alternative reactive ion etch (RIE) processes are very slow and expensive with the inert materials of choice.

In addition to the foregoing, angles of edges of the shaped product article are controlled by the crystal orientation of the above etchants which means some edges and serrations will be non-optimal. Further, 90 degree angles are usually desired at the base of these devices to provide a solid, non-cutting support. The aforementioned etching technique produces razor edges on at least some of those bases making stable mounting of such shaped articles more difficult.

Japanese Patent Kokai No. 63-92345 discloses an edged medical tool wherein the surface of the edge tool is provided with a carbonaceous coating layer of a diamond-like crystalline structure having a thickness of 1 to 20 nm. The diamond-like crystalline structure is deposited by the plasma-induced vapor-phase deposition in an atmosphere of a gaseous mixture of hydrogen and a hydrogen-containing compound such as methane.

U.S. Pat. No. 4,980,021 to Kitamura et al. describes etching of the diamond-like coating layer formed in a process such as that of Japanese Patent Kokai No. 63-92345, with a plasma of hydrogen gas to sufficient extent so that the surface of the edged tool has a roughness of 0.5 to 5 nm. Although this improves the incisiveness of the edged tool, the process starts with an existing shaped base body and therefore does not enable the fabrication of knives with serrations and other cutting variations that are needed in opthalmological surgery.

Microelectronic fabrication techniques have been developed in the field of semiconductors. U.S. Pat. No. 4,916,002 to Carver discloses a microminiature tip assembly which is fabricated using photolithography and anisotropic etching. The crystalline form of silicon is used to advantage by etching along the grain boundaries to form a pit in a silicon substrate. Tungsten is then deposited into the pit to form a sharp tip for use in a scanning tunneling microscope assembly.

Another microfabrication technique is disclosed in U.S. Pat. No. 4,740,410 to Muller, comprising a method of producing a micromechanical structure with two or more members measuring less than 1000 micrometers in any linear dimension. The disclosed technique provides sacrificial layers of material that are later etched away so that the mechanical members become movable relative to each other.

U.S. Pat. No 4,551,192 to DiMillia et al. discloses the use of a silicon carbide body in a pinchuck formed with microcircuit lithography. U.S. Pat. No. 4,911,782 to Brown discloses a miniature biological chamber made with photolithography.

U.S. Pat. No. 5,082,254 to Hunnell, et al. discloses a microtome object holder assembly useful for histology applications, which comprises a clamping member including a V-shaped channel which is formed by electrical discharge machining. Such machining utilizes a reverse image electrode formed of a suitable material such as copper, graphite, copper-tungsten, or the like. The electrical discharge electrode is placed in contact with a metal block to be machined to form a first clamping member. The requisite voltage is applied to produce electrical discharge arcing and erosion of the metal, to form the reverse image of the electrode profile in the resultingly machined metal block. In such manner, discharge electrodes are suitably formed with a reverse image of the desired profile contour, with the electrode being employed to "burn in" the desired contour profile.

Accordingly, it would be a significant advance in the art, and is an object of the present invention, to provide a shaped article and forming technique therefor which overcomes the above-discussed deficiencies, and is broadly applicable to a wide variety of materials of construction.

Another object of the present invention is to provide microsurgical knives in a variety of new and unique shapes, such as serrated knives and concavely shaped knives, and other compound contour shapes.

SUMMARY OF THE INVENTION

The present invention in one method aspect relates to a process for making a microstructural shaped article from a substrate workpiece, comprising the steps of:

(a) providing a metal mold comprising a predetermined shape to be imparted to the substrate workpiece;

(b) securing the metal mold in ultrasonic energy-transmissive relationship to an ultrasonic horn;

(c) providing the substrate workpiece in a fixed position in alignment with the metal mold in ultrasonic energy-transmissive relationship to the ultrasonic horn;

(d) disposing between the metal mold and the substrate a fine grain slurry of solid particles which are energy-transmissive of ultrasonic energy; and (e) ultrasonically milling the substrate workpiece with the ultrasonic horn energized and the metal mold in compressive bearing relationship to the substrate through the fine grain slurry of solid particles disposed between the metal mold and the substrate, for sufficient time to form said predetermined shape in the substrate workpiece.

In the above-identified method, the extent of the ultrasonic milling of the substrate workpiece will depend on the shape to be provided in the product microstructural shaped article. Both 1-sided and 2-sided microstructural shaped articles can be produced by the method of the present invention.

If a 1-sided product article is desired, then the ultrasonic milling can be carried out to completion, through the entire thickness of the substrate workpiece. If a 2-sided product article is desired, then the ultrasonic milling can be carried out only partially through the thickness of the workpiece substrate, and the resulting partially milled substrate workpiece can then be inverted or otherwise alternatively positioned in relation to the first ultrasonic milling step, and subsequently ultrasonically milled in a second ultrasonic milling step, to produce a 2-sided microstructural shaped article.

In like manner, the ultrasonic milling may be carried out with the substrate workpiece fixtured or positioned in various sequentially differing positions, to carry out sequential ultrasonic milling steps as necessary or desirable in a given application of the method of the present invention.

In the use of such multiple milling steps embodiments of the invention, as is suitably employed to produce compound and complex three-dimensional shapes, each of the individual ultrasonic milling steps is suitably carried out with a different metal mold.

The metal mold in the above-identified method may be suitably formed via a process including the steps of:

(i) generating a pattern for the predetermined shape of the microstructural shaped article;

(ii) making an injection mold from the pattern;

(iii) injection molding a plastic material in the injection mold, to yield a plastic pattern;

(iv) sand transfer-molding from the plastic pattern and burning out the injection-molded plastic material to yield the metal mold.

The metal mold also may be provided by forming a plastic mold comprising molding surfaces, as described in steps (i) through (iii) above, followed by plating of the molding surfaces with a suitable metal such as a noble metal, or chromium.

The initial step of generating a pattern for the predetermined shape of the microstructural shaped article may suitably be carried out using three-dimensional photolithography techniques.

In another aspect, the present invention relates to a method in which the milling operation is conducted using energy sources other than ultrasonic or electroacoustic energy sources, such as electric arc machining milling, in which electric power sources may be used to apply a suitable electrical potential to the milling electrode, which is formed of a suitable material, such as graphite, or other electrically conductive material of construction.

The invention in another aspect relates to microstructural shaped articles which are formed by the method of the present invention, and which, being non-etched and non-hand-made in character, overcome the deficiencies of the microstructural shaped articles of the prior art which are formed by etching techniques or manual effort.

In another aspect, the present invention relates to a milling die for use in the method of the invention, wherein the die on a milling surface thereof has a selectively removable tribological coating thereon.

The invention relates in another aspect to a microsurgical instrument comprising an ultrasonically milled cutting surface. Such instrument may for example comprise a knife article having a length of from about 2 to about 20 mm Other aspects, features and embodiments of the invention will be more fully apparent from the ensuing disclosure and appended claims.

BRIEF DESCRIPTION OF THE DRAWINGS

FIG. 1 is a top plan view of a microsurgical knife according to one embodiment of the present invention.

FIG. 2 is a front end elevation view of the microsurgical knife shown in FIG. 1.

FIG. 3 is a rear end elevation view of the microsurgical knife shown in FIG. 1.

FIG. 4 is a side elevational view of a frontal portion of a microsurgical knife according to another embodiment of the invention.

FIG. 7 is a top plan view of a microsurgical knife according to another embodiment of the present invention, and featuring a curvate cutting edge.

FIG. 8 is a top plan view of a spinning saw according to one embodiment of the present invention.

FIG. 9 is a top plan view of a microsurgical knife according to yet another embodiment of the present invention.

FIG. 12 is a top plan view of a pre-shaped blank workpiece for making a microsurgical knife according to another embodiment of the invention.

FIG. 13 is a front edge elevation view of the pre-shaped blank workpiece of FIG. 12.

FIG. 14 is a side elevation view of the pre-shaped blank workpiece of FIG. 12.

FIG. 28 is a top plan view, FIG. 29 is a front elevation view, and FIG. 30 is a side elevation view, of a blade milling tool of a type shown in FIG. 24 and used to form microsurgical knives of the type shown in FIGS. 15–17 from blank workpieces of the type shown in FIGS. 12–14.

DETAILED DESCRIPTION OF THE INVENTION AND PREFERRED EMBODIMENTS THEREOF

Figure 5:
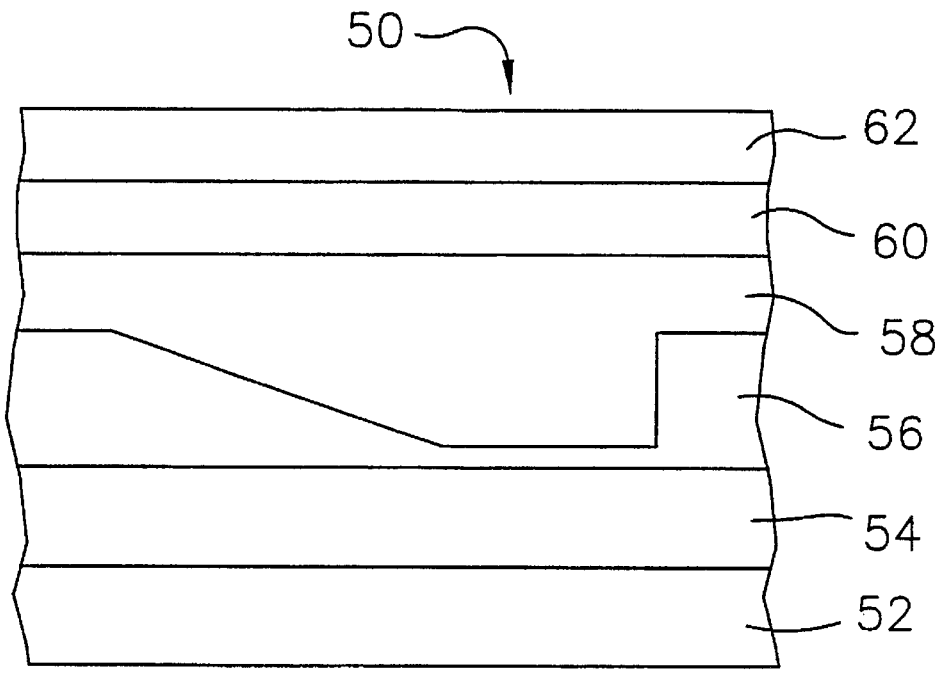
FIG. 5 is a schematic cross-sectional elevation view of an ultrasonic milling assembly for carrying out the method of the present invention, in one embodiment thereof.

The method of the present invention permits microstructural articles to be produced which have a lower manufacturing cost than microstructural product articles formed by handmade techniques. The method of the invention also provides a process for the manufacture of microstructural articles having complex surface artifacts, such as serrated edges, inside angles, and curved surfaces.

The microstructural articles manufacturing method of the present invention uniquely combines several manufacturing techniques to create non-obvious structures which greatly reduce the cost of fabricating microstructural articles, e.g., microsurgical instruments with previously difficult-to-build shapes.

The present invention contemplates a method of making a microstructural shaped article from a substrate workpiece, comprising the steps of:

(a) providing an energy-transmissive shaping member comprising a predetermined shape to be imparted to the substrate workpiece;

(b) securing the energy-transmissive shaping member in energy-transmissive relationship to an energy source;

(c) providing the substrate workpiece in a fixed position in alignment with the energy-transmissive shaping member in energy-transmissive relationship to the energy source;

(d) disposing between the energy-transmissive shaping member and the substrate a fine grain slurry of solid particles which are energy-transmissive of energy) from said energy source; and (e) milling the substrate workpiece with the energy source energized and the energy-transmissive shaping member in compressive bearing relationship to the substrate through the fine grain slurry of solid particles disposed between the energy-transmissive shaping member and the substrate, for sufficient time to form said predetermined shape in the substrate workpiece.

In such method, the energy source may be of any suitable type, but most preferably is an electroacoustic energy source or an electric power energy source, and the shaping member in such most preferred modes of application is suitably an electroacoustically coupled metal die or an electric arc machining electrode, respectively.

The methodology of the invention is usefully employed to produce non-etched and non-hand-made microstructural shaped articles. Such non-etched and non-hand-made microstructural shaped articles may be formed of any suitable material of construction. Presently preferred materials of construction of the substrate workpiece are sapphire, diamond and silicon carbide.

The non-etched and non-hand-made microstructural shaped articles of the invention may comprise any appropriate design, as useful for a given end use application. Examples of articles of the present invention include surgical instruments, micromachinery for fabrication, repair, removal or other operations on small-scale apparatus or articles, prosthetic microimplants for corporeal applications, electronic structures, anti-personnel munitions elements, decorative and aesthetic elements, optical lenses, etc. Particularly preferred microstructural articles of the invention include microsurgical knives.

In a preferred embodiment, the method of the present invention relates to a method of forming microstructural articles from a substrate workpiece, comprising the steps of:

(b) securing the metal mold in ultrasonic energy-transmissive relationship to an ultrasonic horn;

(c) providing the substrate workpiece in a fixed position in alignment with the metal mold in ultrasonic energy-transmissive relationship to the ultrasonic horn;

(d) disposing between the metal mold and the substrate a fine grain slurry of solid particles which are energy-transmissive of ultrasonic energy; and (e) ultrasonically milling the substrate workpiece with the ultrasonic horn energized and the metal mold in compressive bearing relationship to the substrate through the fine grain slurry of solid particles disposed between the metal mold and the substrate, for sufficient time to form said predetermined shape in the substrate workpiece.

In such method, the ultrasonic milling may be conducted through the entire thickness of the substrate workpiece, to produce a 1-sided microstructural shaped article. Alternatively, the ultrasonic milling may be conducted partially through the thickness of the substrate workpiece in a first ultrasonic milling step, and thereafter at least one additional ultrasonic milling step is carried out with the partially ultrasonic milled substrate workpiece in a different position than in the first ultrasonic milling step, to produce a 2-sided microstructural shaped article.

The method of the invention may be carried out with each of the aforementioned at least one additional ultrasonic milling steps being carried out with a different metal mold. Alternatively, the method of the invention may be carried out with the ultrasonic milling being conducted with the substrate workpiece positioned in various sequentially differing positions, to impart compound shapes to the substrate workpiece.

In the above-described method of the invention, the metal mold may suitably be formed by a process including the steps of:

(i) generating a pattern for the predetermined shape of the microstructural shaped article;

(ii) making an injection mold from the pattern;

(iii) injection molding a plastic material in the injection mold to yield a plastic pattern;

(iv) sand transfer-molding from the plastic pattern and burning out the injection-molded plastic material to yield the metal mold.

In this method, the step of generating a pattern for the predetermined shape of the microstructural shaped article may be carried out using any suitable method known in the art for making three-dimensional shapes, e.g., three-dimensional photolithography.

The metal mold also may be provided by forming a plastic mold comprising molding surfaces, as described in steps (i) through (iii) above, followed by plating of the molding surfaces with a suitable metal such as a noble metal, or chromium.

In the method of the present invention, the substrate workpiece may for example be mounted on a base member, e.g., formed of a suitable material such as glass or metal, during the ultrasonic milling. As mentioned, the substrate workpiece may be formed of a material such as sapphire, diamond or silicon carbide. The metal mold may be formed of any suitable metal, as for example a ferrous metal alloy, e.g., steel.

During the milling operation, the substrate workpiece may be bonded to the base member by a cured bondant medium which is solvent soluble, to stationarily fix the substrate workpiece for the milling operation, as well as to provide a support structure accommodating mill-through of the entire thickness of the substrate workpiece.

Where the substrate workpiece is bonded by a suitable bondant medium, the substrate workpiece desirably is removed from the based member subsequent to ultrasonic milling thereof by solvent solubilization of the bondant medium, for removal thereof from the ultrasonically milled substrate workpiece.

In the method of the invention, the fine grain slurry of solid particles which are energy-transmissive of the energy employed in the milling, e.g., ultrasonic energy, may comprise particles of any suitable energy-transmissive material, such as diamond grit or powder. The slurry may comprise any suitable solvent or binder component, such as water, alkanolic or hydrocarbon solvents, etc. The function of the particulate slurry is to provide an abrasive or otherwise millingly effective medium which is suitable for the removal of the substrate to produce the desired patterned product article.

In instances where the substrate workpiece is formed of a material such as carbon or silicon carbide, and the energy employed to mill the substrate workpiece is electrical in character, as in the case of electric arc machining milling of the substrate workpiece, the particulate slurry in some instances may be eliminated as a component of the manufacturing system, but in general the slurry is a necessary and desirable component in instances in which the energy is electroacoustic, e.g., ultrasonic, or electromechanical in character.

Further, the slurry technique may advantageously be employed in "refacing" microsurgical instruments of the instant invention, after a selected period of use, to extend the useful service life of such tools. In this respect, it is to be noted that stainless steel wears at approximately 20% of the wear rate of sapphire under the same wear conditions.

When the slurry technique is employed in the original manufacture of microsurgical articles of the present invention, it may be beneficial to form trenches around the individual articles, e.g., knives or saws, being formed. Such trenches permit diamond grit to flow between successive devices being formed in the substrate workpiece. The ultrasonic or other forming tool may then be lifted from the substrate workpiece and rinsed, followed by reapplication of the diamond grit to the substrate workpiece, and the lowering of the ultrasonic or other forming tool into forming relationship to the substrate workpiece. Such methodology allows the slurry or grit material to be freshened at the surface of the workpiece, thereby enhancing the efficacy of the forming process.

The invention generally utilizes substrate workpieces formed of relatively non-conductive materials such as sapphire, silicon carbide, diamond or diamond-like materials.

The microstructural articles produced by the method of the present invention may be of any suitable structural dimensions, as necessary or desirable in the manufacture and use of such articles. By way of example, the method of the invention may be employed to form microsurgical articles such as scalpels, knives, saws, and the like, which range from about 100 µm to 2000 µm thick and 0.2 to about 3 cm in length. Typically, microsurgical instruments will be from 100 to 1000 µm, and preferably from about 200 to 700 µm, in thickness, to avoid breakage of or damage to the instrument in use, while at the same time providing a highly advantageous thin cutting body.

The method of the invention may be employed to mass produce microstructural articles, utilizing a die or cutting tool which is configured with a patterned milling surface including an array of patterned surface areas, each of which is employed to form an underlying product article in the substrate. The individual patterned surface areas in the patterned array may be the same, for mass production of a same product article, but it is also within the purview of the invention to provide the die or cutting tool with varied pattern areas thereon, so that different microstructural articles can be simultaneously produced.

In such manner, several hundred scalpels, scrapers, or other edged cutting instruments, which may be the same or different from one another, can be mass produced from a single substrate workpiece element, in a batch process. The single substrate workpiece element may be of correspondingly appropriate size for such mass production of instruments. By way of example, when sapphire is employed as a material of construction for the mass-produced instruments, sapphire wafers of 4–6 inches diameter are readily commercially available, and may be usefully employed in the practice of the method of the invention.

Once the microstructural instruments are formed in the substrate, each of the instrument articles may be mounted permanently on a disposable handle, or removably mounted on a reusable handle.

For example, in the case of a microsurgical knife of the type shown in FIG. 1, discussed hereinafter in detail, the stem of a handle member may be sealed on the proximal portion of the knife around the grooves at the proximal end of the knife (see FIG. 1).

Alternatively, the knife, particularly when formed of an optically transparent material, may be mounted on an optical fiber for subsequent use in microsurgery. Such optical fiber may be directly bonded to the proximal portion of the knife with a suitable bondant medium, such as an epoxy resin bondant medium, being provided around the grooves at such proximal portion of the knife.

In the case of circular saws and other microstructural instruments which are rotated in use, a stem or shaft member may be suitably bonded or otherwise secured to the instrument in coaxial relationship to the axis of rotation of the instrument to facilitate the use thereof.

The material of construction of the substrate workpiece may be any suitable material, such as for example: silicon carbide (SIC) of any suitable polytype; silicon; diamond-like materials, optionally subsequently coated with silicon, silicon carbide, or other suitable coating material; sapphire; and metals (e.g., stainless steel). Sapphire, silicon and silicon carbide are currently preferred.

The method of the present invention can produce a wide variety of compound surfaces and complex shapes in the product microstructural articles, including straight (linear), convex, and concave surfaces and shapes. By way of example, serrated edges (e.g., saw-toothed edges, convexly serrated edges, and concavely serrated edges) may be formed, wherein the peaks of the serrations may be extremely close together, as for example from about 25 to about 250 μm apart. The present invention also can produce highly useful convex cutting edges (i.e., convex with respect to plan view of the surgical instrument), including convex cutting edges on reverse cutters.

Referring now to the drawings, FIG. 1 is a top plan view, FIG. 2 is a front end elevation view, and FIG. 3 is a rear end elevation view, of a microsurgical knife 10 according to one embodiment of the present invention. The knife 10 comprises a generally arrowhead-shaped main body portion having a main top surface 12, a main bottom surface 14, rear side surfaces 24 and 26, rear end surface 32, and front beveled surfaces 18 and 20 depending downwardly from the main top surface 12, and intersecting at a distal (frontal) extremity of the knife along the centerline 16. The beveled surfaces 18 and 20 slope downwardly to an outer periphery defining a convergent linear profile along each of the outer margins of the surfaces 18 and 20. Additionally, the beveled surface 20 is provided with a scalloped cutting edge 22 at its outer margin, as shown.

The distal (rear) portion of the knife 10 is notched on each rear side surface 24 and 26 with respective notch cut-outs 28 and 30, to provide a mounting structure accommodating placement of the knife in a suitable holder (not shown, for clarity in FIGS. 1–3).

FIG. 4 is a side elevational view of a frontal portion of a microsurgical knife 40 according to another embodiment of the invention. The knife 40 as shown features a 2-sided pattern, comprising upper and lower tapered surfaces 42 and 44, respectively, which are laterally convergent along the marginal sideline 46.

FIG. 5 is a schematic cross-sectional elevation view of an ultrasonic milling assembly 50 for carrying out the method of the present invention, in one embodiment thereof. The milling assembly 50 comprises, from top to bottom of the illustrated structure, the following constituents parts and elements: an ultrasonic transducer horn 62, a solder layer 62 as a bondant medium securing the horn 62 to a metal milling die 58, a layer 56 of a particulate slurry material, such as a diamond grit in water suspension, a substrate workpiece 54, formed of a suitable millable material such as sapphire or silicon carbide, and a base 52, e.g., of glass, metal or other suitable material of construction, on which the substrate workpiece 54 is disposed, with the workpiece optionally being bonded to the base member by a suitable bondant medium, such as a solvent-soluble adhesive medium.

The milling assembly 50 is shown in FIG. 5 as assembled for milling operation, prior to energization of the ultrasonic horn.

Figure 6:
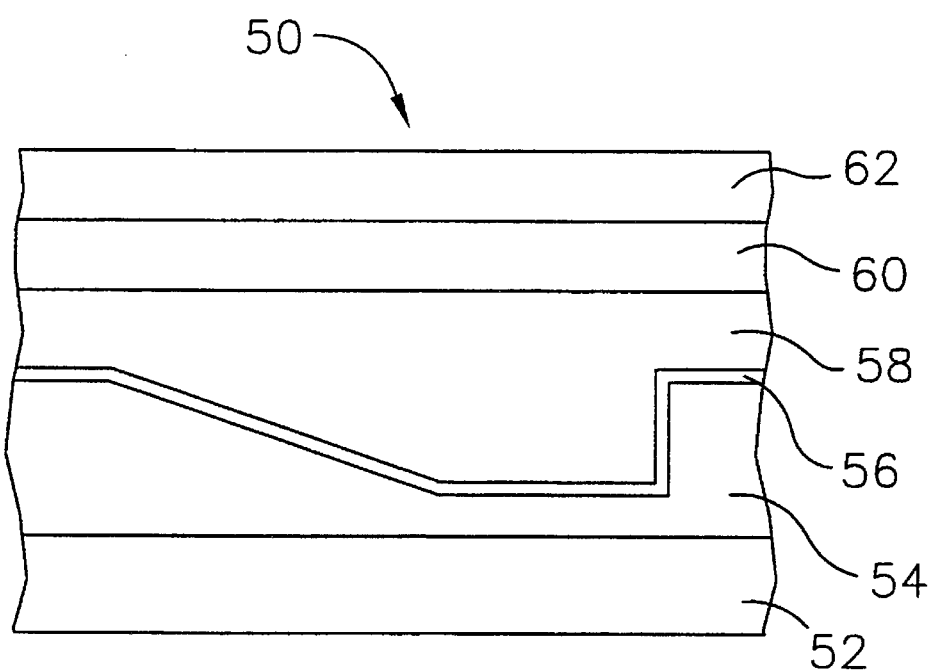
FIG. 6 is a schematic cross-sectional elevation view of the ultrasonic milling assembly of FIG. 5, during a subsequent stage of the ultrasonic milling operation, relative to the initial stage shown in FIG. 5.

The corresponding milling assembly 50 is shown in FIG. 6 with the metal die 58 compressively engaged with the substrate workpiece 54 through the slurry material layer 56 interposed therebetween, to operatively mill the pattern of the die into the substrate and produce a product article of the desired shape and contour. The milling operation as illustrated in FIG. 6 may be carried out only part-way through the substrate workpiece, following which the workpiece may be inverted relative to the orientation shown, and milling recommenced, to produce an opposite corresponding contour to the workpiece and ultimately yield a bi-tapered knife of the form illustratively shown in FIG. 4.

Alternatively, the milling operation may be continued through the entire thickness of the workpiece article, to produce a shaped product article in which a 1-sided patterned and shaped article such as illustratively shown in FIGS. 1–3 is formed.

As mentioned hereinabove, the substrate workpiece may be formed with trenches or cavities surrounding the individual articles being formed in the substrate, e.g., knives or saws, to permit diamond grit to flow thereinto between successive devices being formed in a unitary substrate workpiece. The ultrasonic or other forming tool is sequentially lifted from the substrate workpiece and rinsed, followed by reapplication of diamond grit to the substrate workpiece, and reengagement of the forming tool with the substrate workpiece, to increase the efficiency of the forming process.

FIG. 7 is a top plan view of a microsurgical knife 70 according to another embodiment of the present invention, having a main body portion 74 of curvate character, extending between a distal end 76 and a proximal end 76 thereof, and featuring a curvate cutting edge 72. At the proximal end 76, the main body portion is shaped with opposite marginal cut-outs 78 and 80, to facilitate mounting of the knife in a suitable holder means (not shown).

FIG. 8 is a top plan view of a spinning saw 82 according to one embodiment of the present invention, featuring a central opening 84 and a star-shaped main body portion with beveled edges 86 as illustrated.

FIG. 9 is a top plan view of a microsurgical knife 90 according to yet another embodiment of the present invention. The knife 90 comprises a main central body portion 92 having an array of surface protrusions 94 thereon, with a peripheral knife edge 96 circumscribing the periphery of the knife, with a notched rear portion 98 accommodating mounting means cooperative therewith.

In respect of ultrasonic milling as a milling technique usefully employed in the broad practice of the present invention, the ultrasonic milling system uses a high frequency vertical vibration of small amplitude combined with an abrasive slurry to shape hard and/or brittle materials forming the substrate workpiece. A work tool, usually made of a hard material such as steel in the shape of the features to be milled, drives the abrasive particles in the slurry into the workpiece and removes material by micro-fracturing the workpiece surface. During the process of milling, the tool (die) is also eroded, but usually at a slower rate. In most applications, the tool surface is parallel to the work surface, and tool wear only shortens the length of the tool without changing its shape appreciatively. The tools thus can have reasonably long lifetimes.

If, however, the ultrasonic tool is not parallel to the work surface, as is required to produce non-vertical edge shapes in the workpiece, such as those required for surgical knives, the tool wear is not uniform. The resulting non-uniform wear changes the shape of the workpiece with each successive use. If the edge shape is critical, the tool will have a very limited lifetime. Since tools with compound or other complex shapes are initially more expensive than tools of simple shape, the limitation of a relatively shorter lifetime greatly increases the cost of fabricating parts with non-vertical sidewalls.

The foregoing potential deficiencies of the use of conventional metal machining materials of construction may be advantageously overcome in the practice of the present invention by the provision of a milling die having coated on a milling surface thereof a removable tribological (wear-resistant) material.

More specifically, such die may be provided as an energy-transmissive milling die comprising a predetermined shape on a milling surface thereof to be imparted to a substrate workpiece when the milling die is coupled in energy-transmissive relationship to an energy source, and the shape-bearing milling surface is compressively bearing against the substrate workpiece in operative milling relationship therewith, wherein the die on the milling surface thereof has a selectively removable tribological coating thereon.

The tribological coating is formed of any suitable material, as for example a material selected from the group consisting of metal (e.g., chromium, nickel, high-wear steel, etc.), tribological glasses (e.g., diamond, silicon carbide, etc.), metal carbides (e.g., titanium carbide, molybdenum carbide, etc.), vitreous carbon, and reinforced composite materials (e.g., bronze fiber-reinforced ceramics, graphite fiber-reinforced bismaleimides, etc.).

Figure 10:
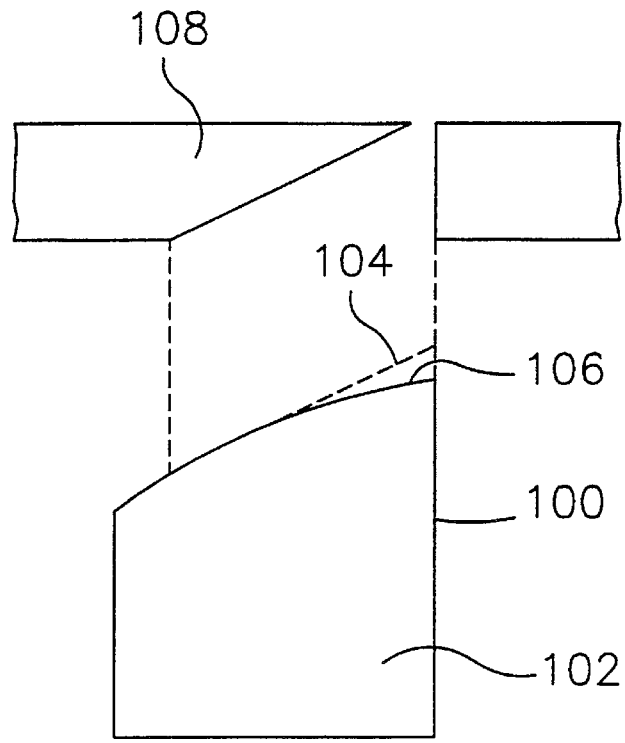
FIG. 10 is a side elevation view of a milling die, showing in dotted line representation the profile of the die surface prior to milling use thereof.

FIG. 10 is a side elevation view of a milling die 100, showing in dotted line representation the profile of the die surface 104 prior to milling use thereof. The die 100 comprises a main body portion 102, and the die is shown in relation to the workpiece substrate 108, with which the die is compressively contacted when the milling die is energized (by coupling with energy source means, not shown for clarity in FIG. 10). After a period of use, the milling die surface is eroded to the surface profile 106, at which point the milling die must be replaced, or reworked, both substantially expensive and undesirable options.

Figure 11:
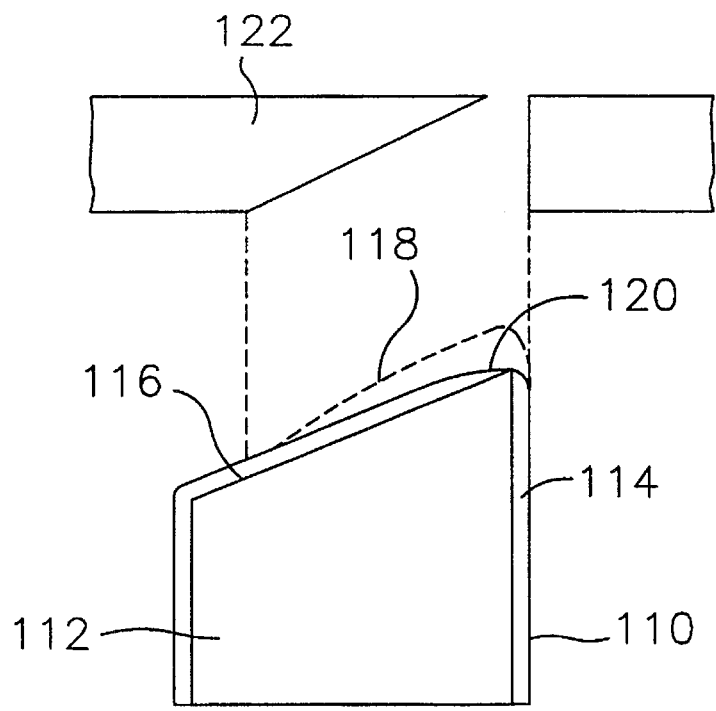
FIG. 11 is a side elevation view of a milling die, having a coating of a tribological material on the milling surface thereof, to accommodate long service life.

FIG. 11 is a side elevation view of a milling die 110 according to one embodiment of the invention, comprising a core main body portion 112 having a coating 114 of a tribological material on the milling surface 116 thereof, to accommodate long service life. The surface profile of the tribological coating 118 after a period of use becomes worn to the profile 120 shown in the drawing, at which time the tribological coating may be suitably removed, by any suitable means and method appropriate to the specific materials of construction of the core main body portion and the tribological coating.

The tribologically enhanced milling die of the invention thus employs a removable tool surface that can virtually eliminate tool replacement in many ultrasonic milling applications, particularly those used to produce workpieces with non-vertical sidewalls. Such milling die comprises a core element that is smaller than the finished size of the tool. This core is made of any suitable hard material, such as tool steel, that is compatible with the coating and removal operations. The milling die may be optionally further enhanced by coating thereof with a diamond-like film coating, to reduce wear of the milling surfaces of the die.

In this respect, it may be advantageous to form the milling die of a relatively softer metal which then is coated with the diamond-like film. The use of a softer metal for such core element of the die will counterintuitively provide a lower wear milling die, than a core element of a relatively harder material coated with a diamond-like film, since the diamond-like film particles will embed in the softer metal to a greater extent than in a relatively harder metal, and impart greater wear resistance to the core element of the softer metal. Accordingly, a soft, "sticky" coating of copper may be usefully employed in the provision of an underlying layer on which the diamond-like film material may be deposited.

A hard material coating is deposited on the core element at a sufficient thickness to enlarge the tool to the proper design size. One example of such a coating method is electroplating which can be used to deposit coatings of nickel, chromium, or other suitable metal materials. Other methods which may be advantageously employed include electroless plating, chemical vapor deposition, flame spraying, plasma spraying, etc.

The dimensions of the core element and the coating are selected such that the total wear for one or more uses of the tool is contained within (accommodated by) the thickness of the coating initially provided on the core element.

After use, the worn coating is selectively removed. Such removal may for example comprise application to the worn tool surface of a chemical etchant that selectively attacks and removes the coating but is non-etching and otherwise inert in relation to the core element. After the worn coating is removed, the tool core element can be recoated and reused.

Since the core element of the die is the most complex and demanding component of the milling structure to fabricate, and represents the major cost in fabricating the tool, the tribologically enhanced die of the present invention achieves a substantial advance, in providing a reusable tool which significantly reduces overall tooling costs, and permits amortization of the tool cost over many milling cycles.

Thus, the present invention provides a tool preparation methodology in which a tool may be milled with many structures, e.g., on a 4-inch wafer substrate, following which a mold is made of the tool. The mold may comprise a sand mold or a plastic mold for use with molten metal. A plastic, ceramic or glass mold may be employed for use with plated metal. The mold is then filled with the appropriate desired metal, and after formation in the mold, the mold is separated (by parting or separation of its component sections, e.g., mold half-sections). The resulting tool may then be optionally refaced using arc milling or equivalent forming techniques, to yield the final product article. The tools typically are used 1–3 times before replacement, with the service life generally being dependent on the tool material(s) of construction, the wear rates encountered in use of the tool, and the design tolerances achieved in the manufacture of the tool.

FIG. 12 is a top plan view of a pre-shaped blank workpiece 200, shown in FIG. 13 in front edge elevation view, and in FIG. 14 in side elevation view, for making a microsurgical knife according to another embodiment of the invention.

As shown in these drawings, the blank workpiece 200 comprises a main body member 205 having a distal portion 201 defined by convergent distal side surfaces 202 and 203 of the main body member, intersecting at the distal extremity 208. The main body member 205 is symmetrical about the longitudinal centerline L—L of the article, and the angle between the longitudinal centerline L—L and each of the distal portion side surfaces 202 and 203 is 15° in the embodiment illustrated.

The main body member 205 also has a proximal portion 204 with inwardly extending (in the direction of the centerline L—L) notches 206, and a proximal end surface 210.

In the illustrative embodiment shown in FIGS. 12–14, the thickness of the main body member may be 0.525 mm, corresponding to a length of the main body member, measured from the proximal end surface 210 to the distal extremity 208, of 10.0 mm. In such illustratively dimensioned embodiment, the notch 206 may be 1.0 mm in length (measured in a direction parallel to the longitudinal centerline L—L) and 0.5 mm deep (measured perpendicularly to the longitudinal centerline L—L), with the longitudinal distance between the notch and the proximal end surface 210 being 1.0 mm. The linear side edge surfaces of the main body member 205 which are parallel to the longitudinal centerline L—L, and proximal to the convergent side surfaces 202 and 203 are 4.4 mm in length, and the width or transverse dimension of the main body member (measured perpendicularly to the longitudinal centerline L—L at the proximal end surface 210) is 3.0 min.

Figure 15:
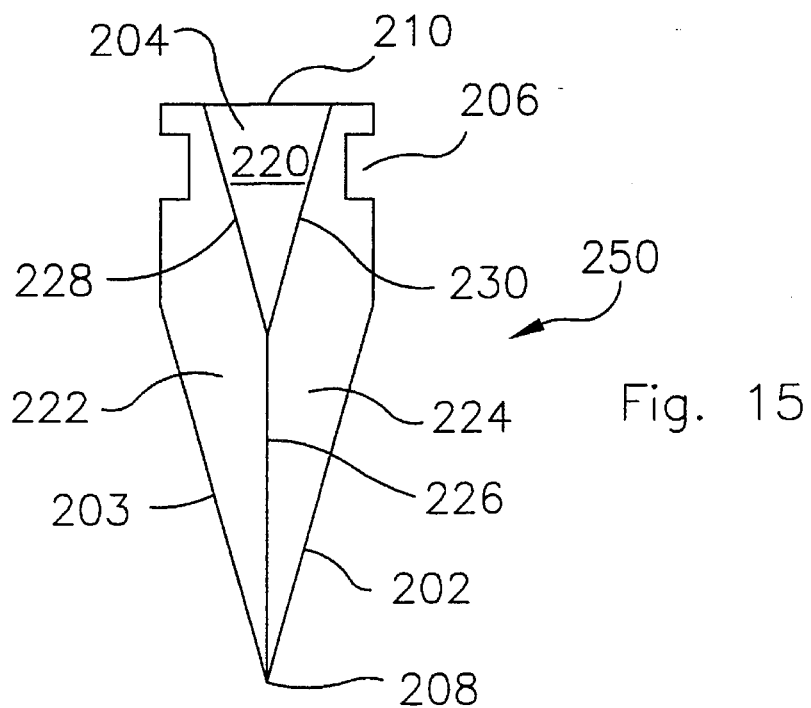
FIG. 15 is a top plan view of a finished microsurgical knife formed from the blank workpiece of FIGS. 12–14.
Figures 16, 17:
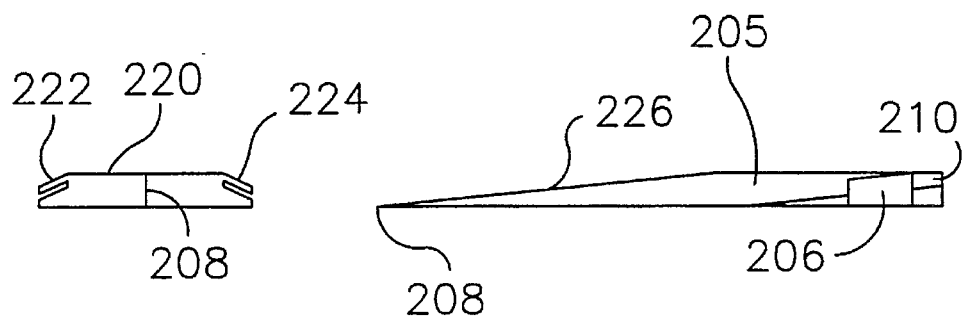
FIG. 16 is a front edge elevation view of the finished microsurgical knife of FIG. 15.
FIG. 17 is a side elevation view of the finished microsurgical knife of FIG. 15.

FIG. 15 is a top plan view of a finished microsurgical knife 250 formed from the blank workpiece of FIGS. 12–14, with the corresponding front edge elevation view being shown in FIG. 16, and the corresponding side elevation view being shown in FIG. 17. In the FIGS. 15–17 views, the parts and elements of the finished knife are numbered correspondingly with respect to the knife blank of FIGS. 12–14.

As shown in FIGS. 15–17, the knife has been formed from the corresponding blank workpiece, by milling of the workpiece to the shape illustrated, comprising a main top surface 220 bounded by distally convergent margins 228 and 230. Between these respective margins and the side edges 202 and 203 of the knife, there are provided downwardly slanting knife surfaces 222 and 224 intersecting at the centerline boundary 226. As shown in the side elevation view of FIG. 17, the knife in side profile has a stiletto conformation, and the angle formed between the centerline boundary 226 and the flat bottom surface of the knife is 6.0°. The knife article may for example have a length of from about 2 to about 20 mm. corresponding to the length along the longitudinal centerline from the proximal end extremity to the distal end extremity (the actual knife edge length typically constitutes from about 20% to about 85% of such overall length of the knife article).

Figure 18:
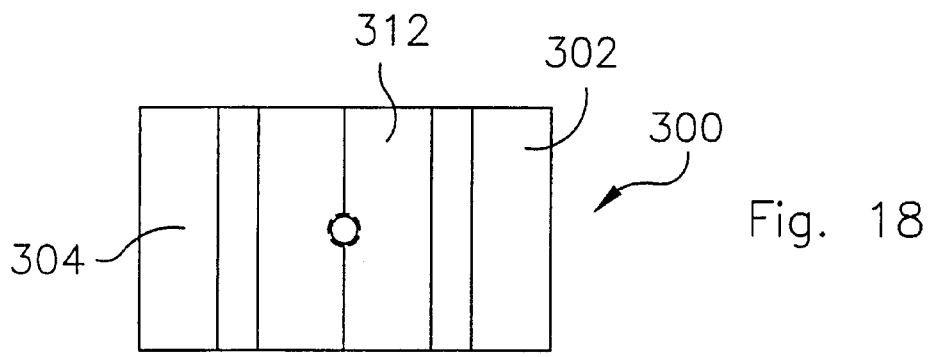
FIG. 18 is a top plan view.
Figures 19, 20:
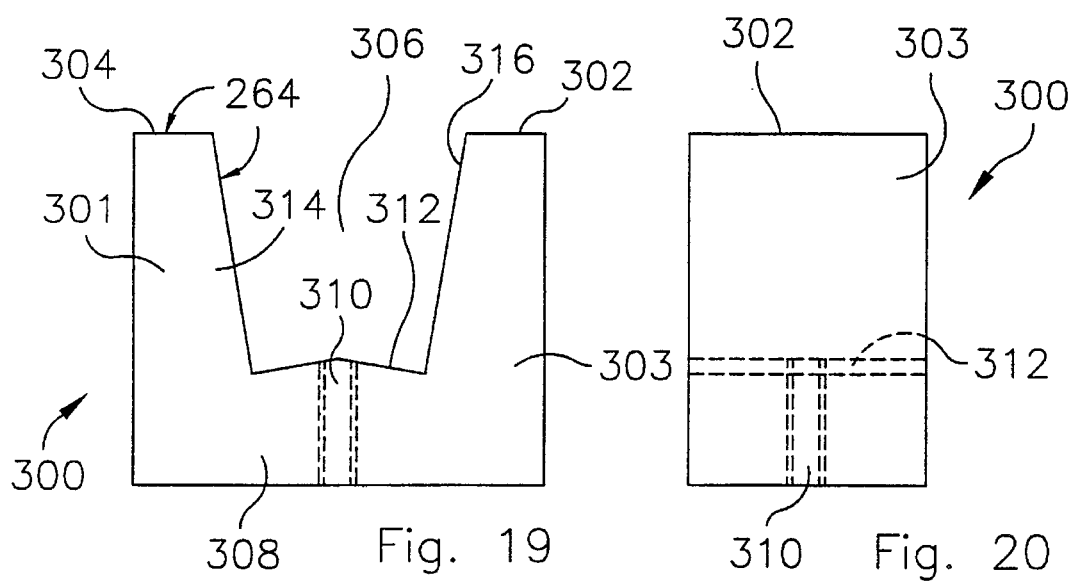
FIG. 19 is a front elevation view.
FIG. 20 is a side elevation view, of a support fixture for use in making microsurgical knives of the type shown in FIGS. 15–17 from blank workpieces of the type shown in FIGS. 12–14.

FIG. 18 is a top plan view, FIG. 19 is a front elevation view, and FIG. 20 is a side elevation view, of a support fixture 300 for use in making microsurgical knives of the type shown in FIGS. 15–17 from blank workpieces of the type shown in FIGS. 12–14.

The support fixture 300 is of generally U-shape, as shown in the elevation view of FIG. 19, comprising leg members 301 and 303 upwardly extending from the base member 308 to respective upper (top) surfaces 304 and 302, to define an interior fixture volume 306 bounded by the inner facing wall surfaces 314 and 316 of the respective leg members 301 and 303, and the floor surface 312 of the base member 308. The base member 308 has a threaded fastener opening 310 formed therein, for securement of substrate workpieces in the fixture as will be described hereinafter in greater detail.

Figure 21:
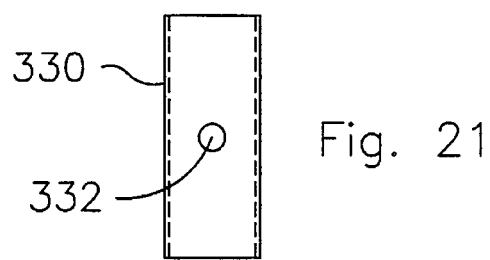
FIG. 21 is a top plan view.
Figures 22, 23:
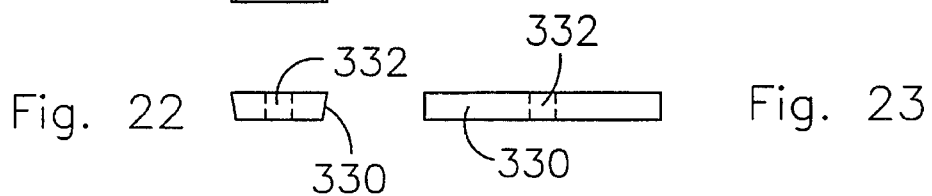
FIG. 22 is a front elevation view.
FIG. 23 is a side elevation view, of a fixture insert member for use with the support fixture of FIGS. 18–20.

FIG. 21 is a top plan view, FIG. 22 is a front elevation view, and FIG. 23 is a side elevation view, of a fixture insert member 330 for use with the support fixture of FIGS. 18–20. The fixture insert member 330 has a threaded fastener opening 332 therein, which may be of a corresponding diameter to the threaded fastener opening 310 in the base member 308 of the support fixture shown in FIGS. 18–20. These openings 310 and 332 may be suitably tapped or otherwise threaded to matably threadably engage the fastener as hereinafter more fully described.

Figure 24:
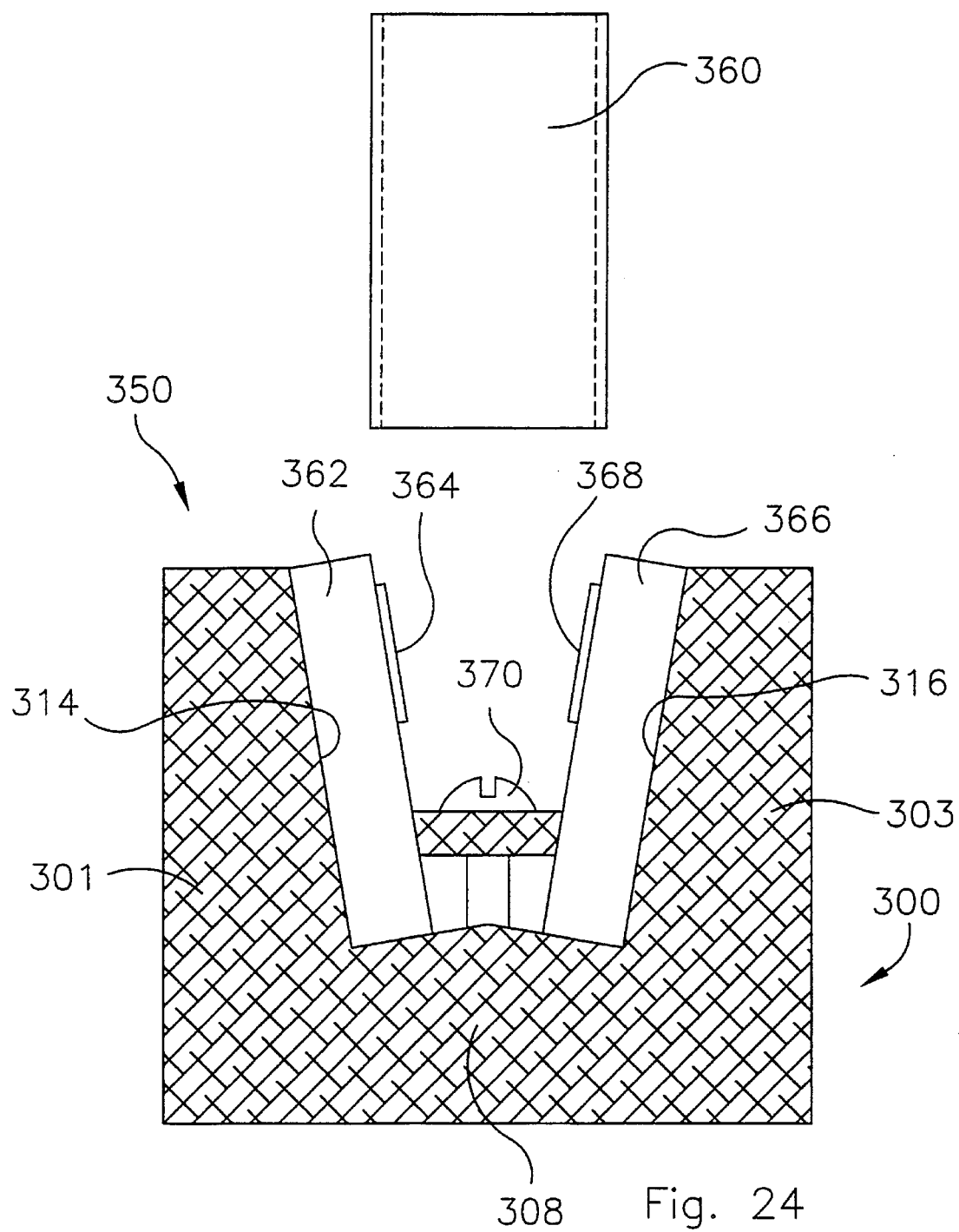
FIG. 24 is a front elevation view of a fixture assembly and blade milling tool shown in operative relationship to one another, for forming microsurgical knife articles.

FIG. 24 is a front elevation view of a fixture assembly 350 and blade milling tool 360 shown in operative relationship to one another, for forming microsurgical knife articles. The fixture assembly 350 comprises a support fixture 300 as shown in FIGS. 18–20, and a fixture insert member 330 as shown in FIGS. 21–23, wherein all corresponding parts and elements are numbered correspondingly with respect to FIGS. 18–23.

In the FIG. 24 forming apparatus, the fixture insert member 330 is threadably secured to the base member of the support fixture 300 (in threaded opening 310 of the base member (not shown in FIG. 24; see FIGS. 18–20)) by mans of threaded fastener 370, with the side edges of the fixture insert member being in abutting and bearing contact relationship with the workpiece support members 362 and 366, to retain the workpiece support members in fixed position in the support fixture for contact of the forming, e.g., milling, tool 360 with the workpieces 364 and 368 fixedly mounted on the workpiece support members 362 and 366 (by means such as an adhesive bondant medium).

The workpiece support members 362 and 366 are formed of any suitable material of construction, such as for example glass or ceramic, and the workpieces mounted thereon may be for example knife blanks of a type shown in FIGS. 12–14, in which case the forming tool 360 may suitably comprise a milling tool shaped to form the finished knife articles of the type shown in FIGS. 15–17. Alternatively, the workpieces may be precursor workpiece block elements which are formed by the forming tool 360 into knife blanks of the type shown in FIGS. 12–14, in which case the forming tool may suitably comprise a blade cutout tool, as hereinafter more fully described.

In operation of the forming assembly shown in FIG. 24, the forming tool is operatively arranged with respect to actuating and forming means, e.g., ultrasonic drivers, not shown in the FIG. 24 schematic drawing, and the tool 360 then is selectively and controllably brought into forming contact with the workpieces 364 and 366 mounted on the workpiece support members 362 and 366.

Figure 25:
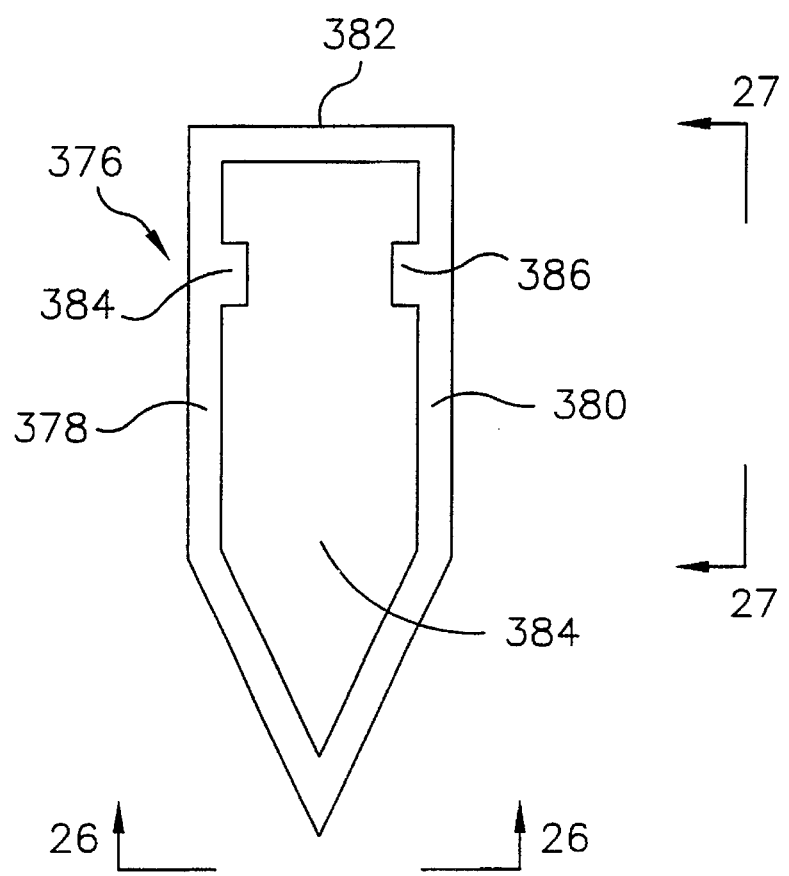
FIG. 25 is a top plan view.
Figure 26:
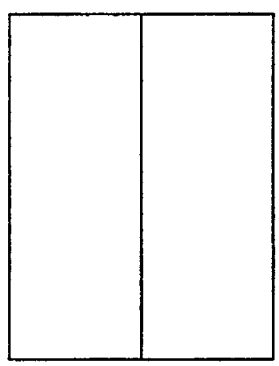
FIG. 26 is a front elevation view.
Figure 27:
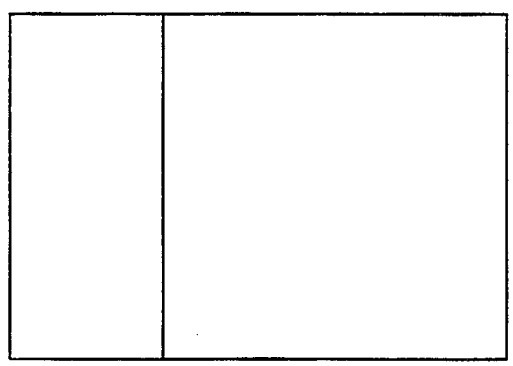
FIG. 27 is a side elevation view, of a blade cutout tool, for forming a knife blank of the type shown in FIGS. 12–14 from a substrate workpiece.

FIG. 25 is a top plan view, FIG. 26 is a front elevation view, and FIG. 27 is a side elevation view, of a blade cutout tool 376, for forming a knife blank of the type shown in FIGS. 12–14 from substrate workpieces of a block precursor form as mountable on workpiece support members as shown in the schematic drawing of the forming apparatus in FIG. 24.

FIG. 25 shows the blade cutout tool 376 as being of generally knife-shape, comprising the leg members 378 and 380 joined at respective corresponding extremeties to the yoke member 382 as shown. The respective leg and yoke members thereby define an interior space 384 bounded by the interior wall surfaces of these leg and yoke members, with the leg members having inwardly extending flange elements 384 and 386 protruding from the interior wall surfaces of the leg members into the interior space 384.

The cutout tool 376 shown in FIGS. 25–27 may be usefully employed to form a knife blank of the type shown in FIGS. 12–14 from a corresponding substrate workpiece. Following such formation, the knife blank may then be further formed into the finished knife of the type shown in FIGS. 15–17 using the blade milling tool 390 shown in FIG. 28 in top plan view, in FIG. 29 in front elevation view, and in FIG. 30 in side elevation view.

As illustrated in FIG. 28–30, the blade milling tool 390 comprises a main body portion with front and back surfaces 398 and 399, respectively, and top and bottom surfaces 400 and 402. The end surfaces comprise downwardly slanting linear surfaces 392 and 394 extending convergently and interiorly into the main body portion of the tool, and intersecting at trough line 396.

The blade milling tool 390 shown in FIGS. 28–30 may be employed to form a knife blank of the type shown in FIGS.

12–14 into the finished knife of the type shown in FIGS. 15–17, in a forming assembly of the type shown in FIG. 24, wherein the blade milling tool constitutes the forming tool 360 schematically shown in FIG. 24.

While the invention has been illustratively described herein, in reference to specific features, aspects, and embodiments, it will be recognized that the invention is susceptible to being practiced in a wide range of variations, modifications, and other embodiments, and it therefore will be recognized that the invention encompasses all such alternative variations, modifications, and other embodiments, within its spirit and scope.

What is claimed is:

1. A method of making a microstructural shaped article from a substrate workpiece, comprising the steps of:
   (a) providing a metal mold comprising a predetermined shape to be imparted to the substrate workpiece;
   (b) securing the metal mold in ultrasonic energy-transmissive relationship to an ultrasonic horn;
   (c) providing the substrate workpiece in a fixed position in alignment with metal mold in ultrasonic energy-transmissive relationship to an ultrasonic horn;
   (d) disposing directly between the metal mold and the substrate workpiece only a fine grain slurry of solid particles which are energy-transmissive of ultrasonic energy; and
   (e) ultrasonically milling the substrate workpiece with the ultrasonic horn energized and the metal mold in direct compressive bearing relationship to the substrate through the fine grain slurry of solid particles disposed directly between the metal mold and the workpiece substrate, for sufficient time to form said predetermined shape in the substrate workpiece.

2. A method according to claim 1, wherein the ultrasonic milling is conducted through the entire thickness of the substrate workpiece, to produce a 1-sided microstructural shaped article.

3. A method according to claim 1, wherein the ultrasonic milling is conducted partially through the thickness of the substrate workpiece in a first ultrasonic milling step, and thereafter at least one additional ultrasonic milling step is carried out with the partially ultrasonic milled substrate workpiece in a different position than in the first ultrasonic milling step, to produce a 2-sided microstructural shaped article.

4. A method according to claim 3, wherein each of the at least one additional ultrasonic milling steps is carried out with a different metal mold.

5. A method according to claim 1, wherein the ultrasonic milling is carried out with the substrate workpiece positioned in various sequentially differing positions, to impart compound shapes to the substrate workpiece.

6. A method according to claim 1, wherein the metal mold is formed by a process including the steps of:
   (i) generating a pattern for the predetermined shape of the microstructural shaped article;
   (ii) making an injection mold from the pattern;
   (iii) injection molding a plastic material in the injection mold to yield a plastic pattern;
   (iv) sand transfer-molding from the plastic pattern and burning out the injection-molded plastic material to yield the metal mold.

7. A method according to claim 6, wherein the step of generating a pattern for the predetermined shape of the microstructural shaped article is carried out using three-dimensional photolithography.

8. A method according to claim 1, wherein the metal mold is provided by forming a plastic mold comprising molding surfaces, and plating said molding surfaces with a metal selected from the group consisting of noble metals and chromium.

9. A method of making a microstructural shaped article from a substrate workpiece, comprising the steps of:
   (a) providing a metal mold comprising a predetermined shape to be imparted to the substrate workpiece;
   (b) securing the metal mold in ultrasonic energy-transmissive relationship to an ultrasonic horn;
   (c) providing the substrate workpiece in a fixed position in alignment with the metal mold in ultrasonic energy-transmissive relationship to an ultrasonic horn;
   (d) disposing between the metal mold and the substrate a fine grain slurry of solid particles which are energy-transmissive of ultrasonic energy; and
   (e) ultrasonically milling the substrate workpiece with the ultrasonic horn energized and the metal mold in compressive bearing relationship to the substrate through the fine grain slurry of solid particles disposed between the metal mold and substrate, for sufficient time to form said predetermined shape in the substrate workpiece, wherein said substrate workpiece is mounted on a base member during said ultrasonic milling.

10. A method according to claim 9, wherein the base member is formed of a material selected from the group consisting of glass and metal.

11. A method according to claim 10, wherein the substrate workpiece is formed of a material selected from the group consisting of sapphire, diamond-like material, aluminum nitride, boron carbide, and silicon carbide.

12. A method according to claim 1, wherein the metal mold is formed of a ferrous alloy material.

13. A method according to claim 9, wherein the substrate workpiece is bonded to the base member by a cured bondant medium which is solvent soluble.

14. A method according to claim 13, wherein the substrate workpiece is removed from the base member subsequent to ultrasonic milling thereof by solvent solubilization of the bondant medium for removal thereof from the ultrasonically milled substrate workpiece.

15. A method according to claim 1, wherein the fine grain slurry of solid particles which are energy-transmissive of ultrasonic energy, comprises particles of a material selected from the group consisting of diamond and metals.

16. A method of making a microstructural shaped article of a predetermined shape from a substrate workpiece, comprising the steps of:
   (a) providing an energy-transmissive shaping member comprising a metal die or a machining electrode;
   (b) securing the energy-transmissive shaping member in energy-transmissive relationship to an energy source;
   (c) providing the substrate workpiece in a fixed position in alignment with the energy-transmissive shaping member in an energy-transmissive relationship to the energy source;
   (d) disposing directly between the energy-transmissive shaping member and the substrate workpiece only a fine grain slurry of solid particles which are energy-transmissive of energy from said energy source; and
   (e) milling the substrate workpiece with the energy source energized and the energy-transmissive shaping member in direct compressive bearing relationship to the substrate through the fine grain slurry of solid particles disposed directly between the energy-transmissive shaping member and the workpiece substrate, for sufficient time to form said predetermined shape in the substrate workpiece.

17. A method according to claim 16, wherein the energy source is selected from the group consisting of electroacoustic energy sources and electric power energy sources, and the shaping member is selected from the group consisting of electroacoustically coupled metal dies and electric arc machining electrodes, respectively.

18. A non-etched and non-hand-made microstructural shaped article made by the method of claim 16.

19. A non-etched and non-hand-made microstructural shaped article made by the method of claim 1.

20. A non-etched and non-hand-made microstructural shaped article according to claim 19, wherein the article is formed of a material of construction selected from the group consisting of sapphire, diamond and silicon carbide.

21. A non-etched and non-hand-made microstructural shaped article according to claim 19, wherein the article comprises a microsurgical knife.

* * * * *